(12) United States Patent
Nguyen-Stella et al.

(10) Patent No.: US 9,352,147 B2
(45) Date of Patent: May 31, 2016

(54) TORQUE LOCK ANCHOR AND METHODS AND DEVICES USING THE ANCHOR

(75) Inventors: Quynh Nguyen-Stella, Palmdale, CA (US); Kenny Kinyen Chinn, Castaic, CA (US); John Michael Barker, Ventura, CA (US); Surekha B. Husmann, Los Angeles, CA (US); Roger Chen, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 251 days.

(21) Appl. No.: 13/022,415

(22) Filed: Feb. 7, 2011

(65) Prior Publication Data

US 2011/0178573 A1    Jul. 21, 2011

Related U.S. Application Data

(63) Continuation-in-part of application No. 12/430,304, filed on Apr. 27, 2009.

(51) Int. Cl.
*A61N 1/05* (2006.01)
*A61N 1/36* (2006.01)
(Continued)

(52) U.S. Cl.
CPC ............... *A61N 1/0558* (2013.01); *H01R 4/36* (2013.01); *A61N 1/057* (2013.01); *A61N 1/0551* (2013.01); *H01R 24/58* (2013.01); *H01R 2201/12* (2013.01)

(58) Field of Classification Search
CPC ..... A61N 1/05; A61N 1/0551; A61N 1/0558; A61N 1/057; A61N 1/059; A61N 2001/0582; A61M 25/02; H01R 2201/12; H01R 4/36; H01R 24/58

USPC ............... 607/115, 116, 117, 119, 122, 126; 604/174, 175

See application file for complete search history.

(56) References Cited

U.S. PATENT DOCUMENTS

| 3,866,615 A | 2/1975 | Hewson |
| 4,141,752 A | 2/1979 | Shipko |

(Continued)

FOREIGN PATENT DOCUMENTS

| EP | 85417 A1 | 8/1983 |
| EP | 0597213 A1 | 5/1994 |

(Continued)

OTHER PUBLICATIONS

International Search Report and Written Opinion for International Patent Application No. PCT/US2012/023931 mailed Mar. 27, 2012.

(Continued)

*Primary Examiner* — Theodore Stigell
*Assistant Examiner* — Pamela M Bays
(74) *Attorney, Agent, or Firm* — Lowe Graham Jones PLLC; Bruce E. Black

(57) ABSTRACT

A lead anchor includes a body defining a lead lumen having a first opening and a second opening through which a lead can pass. The body further defines a transverse lumen that intersects the lead lumen. An exterior member is disposed around at least a portion of the body. The exterior member is formed of a biocompatible material. A fastener anchors the lead to the body through the transverse lumen by deforming a portion of the lead. The transverse lumen is configured and arranged to receive the fastener. At least at least two suture tabs extend from the exterior member and are configured and arranged for receiving a suture to suture the lead anchor to patient tissue.

20 Claims, 16 Drawing Sheets

(51) Int. Cl.
*H01R 4/36* (2006.01)
*H01R 24/58* (2011.01)

(56) References Cited

U.S. PATENT DOCUMENTS

| | | | |
|---|---|---|---|
| 4,276,882 A | 7/1981 | Dickhudt et al. | |
| 4,316,471 A | 2/1982 | Shipko et al. | |
| 4,462,401 A | 7/1984 | Burgio | |
| 4,632,670 A | 12/1986 | Mueller, Jr. | |
| 4,764,132 A | 8/1988 | Stutz, Jr. | |
| 4,858,623 A | 8/1989 | Bradshaw et al. | |
| 5,036,862 A * | 8/1991 | Pohndorf | 607/122 |
| 5,107,856 A | 4/1992 | Kristiansen et al. | |
| 5,158,097 A | 10/1992 | Christlieb | |
| 5,228,248 A | 7/1993 | Haddock | |
| 5,376,108 A | 12/1994 | Collins et al. | |
| 5,484,445 A | 1/1996 | Knuth | |
| 5,746,722 A * | 5/1998 | Pohndorf et al. | 604/175 |
| 5,865,843 A | 2/1999 | Baudino | |
| 5,957,968 A | 9/1999 | Belden et al. | |
| 6,181,969 B1 | 1/2001 | Gord | |
| 6,192,279 B1 | 2/2001 | Barreras, Sr. et al. | |
| 6,360,750 B1 | 3/2002 | Gerber et al. | |
| 6,473,654 B1 * | 10/2002 | Chinn | 607/126 |
| 6,516,227 B1 | 2/2003 | Meadows et al. | |
| 6,606,523 B1 | 8/2003 | Jenkins | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,792,314 B2 | 9/2004 | Byers et al. | |
| 6,847,849 B2 | 1/2005 | Mamo et al. | |
| 6,901,287 B2 | 5/2005 | Davis et al. | |
| 6,978,180 B2 | 12/2005 | Tadlock | |
| 6,984,145 B1 | 1/2006 | Lim | |
| 7,069,083 B2 | 6/2006 | Finch et al. | |
| 7,072,719 B2 | 7/2006 | Vinup et al. | |
| 7,161,461 B1 | 1/2007 | Nelson | |
| 7,244,150 B1 | 7/2007 | Brase et al. | |
| 7,343,202 B2 | 3/2008 | Mrva et al. | |
| 7,437,193 B2 | 10/2008 | Parramon et al. | |
| 7,447,546 B2 | 11/2008 | Kim et al. | |
| 7,672,734 B2 | 3/2010 | Anderson et al. | |
| 7,761,165 B1 | 7/2010 | He et al. | |
| 7,787,960 B2 | 8/2010 | Lubenow | |
| 7,848,803 B1 | 12/2010 | Jaax et al. | |
| 7,853,321 B2 | 12/2010 | Jaax et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,224,451 B2 | 7/2012 | Jaax et al. | |
| 8,229,573 B2 | 7/2012 | Chen et al. | |
| 8,315,704 B2 | 11/2012 | Jaax et al. | |
| 8,364,278 B2 | 1/2013 | Pianca et al. | |
| 2001/0000187 A1 | 4/2001 | Peckham et al. | |
| 2002/0107554 A1 | 8/2002 | Biggs et al. | |
| 2003/0078623 A1 | 4/2003 | Weinberg et al. | |
| 2003/0208247 A1 | 11/2003 | Spinelli et al. | |
| 2004/0059392 A1 | 3/2004 | Parramon et al. | |
| 2005/0165465 A1 | 7/2005 | Pianca et al. | |
| 2005/0283202 A1 | 12/2005 | Gellman | |
| 2005/0288760 A1 | 12/2005 | Machado et al. | |
| 2006/0127158 A1 | 6/2006 | Olson et al. | |
| 2006/0161235 A1 | 7/2006 | King | |
| 2006/0173520 A1 * | 8/2006 | Olson | 607/115 |
| 2006/0206162 A1 | 9/2006 | Wahlstrand et al. | |
| 2007/0050005 A1 | 3/2007 | Lauro | |
| 2007/0078399 A1 | 4/2007 | Olson | |
| 2007/0150036 A1 | 6/2007 | Anderson | |
| 2007/0219595 A1 | 9/2007 | He | |
| 2007/0255369 A1 | 11/2007 | Bonde et al. | |
| 2008/0071320 A1 | 3/2008 | Brase | |
| 2008/0091255 A1 | 4/2008 | Caparso et al. | |
| 2008/0140169 A1 | 6/2008 | Imran | |
| 2008/0172116 A1 | 7/2008 | Mrva et al. | |
| 2008/0183241 A1 | 7/2008 | Bedenbaugh | |
| 2008/0183253 A1 | 7/2008 | Bly | |
| 2008/0196939 A1 * | 8/2008 | Lubenow et al. | 174/652 |
| 2008/0228251 A1 | 9/2008 | Hill | |
| 2008/0243220 A1 | 10/2008 | Barker | |
| 2008/0312712 A1 | 12/2008 | Penner | |
| 2009/0018601 A1 | 1/2009 | Deininger et al. | |
| 2009/0112272 A1 | 4/2009 | Schleicher et al. | |
| 2009/0198312 A1 | 8/2009 | Barker | |
| 2009/0254151 A1 | 10/2009 | Anderson et al. | |
| 2009/0270940 A1 | 10/2009 | Deininger | |
| 2010/0174240 A1 | 7/2010 | Wells et al. | |
| 2010/0274336 A1 | 10/2010 | Nguyen-Stella et al. | |
| 2010/0312319 A1 | 12/2010 | Barker et al. | |
| 2011/0022142 A1 | 1/2011 | Barker et al. | |
| 2011/0060395 A1 | 3/2011 | Cantlon | |
| 2011/0178573 A1 | 7/2011 | Nguyen-Stella et al. | |
| 2012/0150202 A1 | 6/2012 | Chen et al. | |
| 2012/0232626 A1 | 9/2012 | Daglow | |
| 2012/0277670 A1 | 11/2012 | Goetz | |
| 2012/0330355 A1 | 12/2012 | Finley et al. | |
| 2013/0204336 A1 | 8/2013 | Sharma | |
| 2015/0246216 A1 | 9/2015 | Barker | |

FOREIGN PATENT DOCUMENTS

| | | |
|---|---|---|
| WO | WO-9833551 A1 | 8/1998 |
| WO | 99/53994 | 10/1999 |
| WO | 00/13743 A2 | 3/2000 |
| WO | 00/64535 | 11/2000 |
| WO | 0064535 | 11/2000 |
| WO | WO-0064535 A1 | 11/2000 |
| WO | 2004/054655 | 7/2004 |
| WO | 2006/086363 A2 | 8/2006 |
| WO | 2007/056384 A2 | 5/2007 |
| WO | 2007/083108 A2 | 7/2007 |
| WO | 2007/149994 A2 | 12/2007 |
| WO | 2008/094789 A1 | 8/2008 |
| WO | 2008101026 A1 | 8/2008 |
| WO | 2008/121708 A2 | 10/2008 |
| WO | 2010/126853 A1 | 11/2010 |
| WO | 2013112920 A1 | 8/2013 |

OTHER PUBLICATIONS

Official Communication U.S. Appl. No. 12/430,304 mailed Mar. 14, 2012.
International Search Report for International Patent Application No. PCT/US2010/032480 mailed Aug. 27, 2010.
U.S. Appl. No. 12/430,304, Official Communication mailed Sep. 24, 2012.
U.S. Appl. No. 12/430,304, Official Communication mailed Mar. 27, 2013.
International Search Report and Written Opinion for International Application No. PCT/US2013/033180 mailed Sep. 19, 2013.
U.S. Appl. No. 12/430,304 Official Communication mailed Jun. 4, 2013.
U.S. Appl. No. 12/430,304 Appeal Brief filed Oct. 30, 2013.
U.S. Appl. No. 13/427,679 Official Communication mailed Jul. 1, 2013.
U.S. Appl. No. 13/427,679 Official Communication mailed Dec. 27, 2013.
U.S. Appl. No. 14/457,602, filed Aug. 12, 2014.
U.S. Appl. No. 14/452,467, filed Aug. 5, 2014.
U.S. Appl. No. 14/457,640, filed Aug. 12, 2014.
U.S. Appl. No. 14/312,194, filed Jun. 23, 2014.
Official Communication for U.S. Appl. No. 13/427,679 mailed Aug. 13, 2014.
Official Communication for U.S. Appl. No. 12/430,304 mailed Jan. 13, 2015.
Official Communication for U.S. Appl. No. 12/430,304 mailed Jun. 3, 2014.
Official Communication for U.S. Appl. No. 12/430,304 mailed Feb. 19, 2014.
Official Communication for U.S. Appl. No. 13/427,679 mailed Dec. 30, 2014.

* cited by examiner

TORQUE LOCK ANCHOR AND METHODS AND DEVICES USING THE ANCHOR

CROSS-REFERENCE TO RELATED APPLICATIONS

This patent application is a continuation-in-part of U.S. patent application Ser. No. 12/430,304, filed Apr. 27, 2009, which is incorporated herein by reference.

FIELD

The invention is directed to lead anchors for implantable devices, as well as the implantable devices themselves, and methods of manufacture and use of the lead anchors and implantable devices. The invention is also directed to lead anchors for implantable spinal cord stimulators, as well as the implantable spinal cord stimulators, and methods of manufacture and use of the lead anchors and the implantable spinal cord stimulators.

BACKGROUND

Spinal cord stimulation is a well accepted clinical method for reducing pain in certain populations of patients. Implantable stimulation devices have been developed to provide therapy for a variety of treatments. For example, implantable stimulation devices can be used to stimulate nerves, such as the spinal cord, muscles, or other tissue. An implantable stimulation device typically includes an implanted control module (with a pulse generator), a lead, and an array of stimulator electrodes. The stimulator electrodes are implanted in contact with or near the nerves, muscles, or other tissue to be stimulated. The pulse generator in the control module generates electrical pulses that are delivered by the electrodes to body tissue. As an example, electrical pulses can be provided to the dorsal column fibers within the spinal cord to provide spinal cord stimulation.

The stimulator electrodes are coupled to the control module by the lead and the control module is implanted elsewhere in the body, for example, in a subcutaneous pocket. The lead is often anchored at one or more places in the body to prevent or reduce movement of the lead or stimulator electrodes within the body which could damage tissue, move the stimulator electrodes out of the desired position, or interrupt the connection between the stimulator electrodes and the control module.

Many conventional lead anchors do not sufficiently grip the lead to keep the lead in place. According to recent studies, lead migration occurs in approximately 13% of cases. Additional studies suggest that electrode migration may be the most common reason for failure to maintain long-term pain control with spinal cord stimulation. Other problems associated with lead migration include lead breakage, and loose connection.

Yet another problem associated with conventional lead anchors is that they are typically anchored at one or more places in the body to prevent or reduce movement of the lead by securing the anchor using sutures. These anchors are highly dependent on suturing technique and lead to variable holding forces. Depending on the physician, the suturing of the lead to the anchor may be too loose or too tight. Furthermore, the increased suturing may lead to an increased operation time with a greater risk of infection.

BRIEF SUMMARY

In one embodiment, a lead anchor includes a body defining a lead lumen having a first opening and a second opening through which a lead can pass. The body further defines a transverse lumen that intersects the lead lumen. The transverse lumen is configured and arranged to receive a fastener. An exterior member is disposed around at least a portion of the body. The exterior member is formed of a biocompatible material. The fastener anchors the lead to the body through the transverse lumen by deforming a portion of the lead. At least at least two suture tabs extend from the exterior member and are configured and arranged for receiving a suture to suture the lead anchor to patient tissue.

In another embodiment, a method of implanting an implantable stimulation device includes implanting an electrode array near tissue to be stimulated. An anchor is disposed around a portion of the lead. The anchor includes a body defining a lead lumen having a first opening and a second opening through which a lead can pass. The body further defines a transverse lumen that intersects the lead lumen. An exterior member is disposed around at least a portion of the body. The exterior member is formed of a biocompatible material. A fastener anchors the lead to the body through the transverse lumen by deforming a portion of the lead. The transverse lumen is configured and arranged to receive the fastener. At least at least two suture tabs extend from the exterior member and are configured and arranged for receiving a suture to suture the lead anchor to patient tissue. The fastener is tightened to secure the anchor to the lead. Sutures secure the anchor to the surrounding tissue.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of lead anchors used with elongate implantable devices such as spinal cord leads, cardiac pacing leads or catheters, implantable devices or systems containing the lead anchors, methods of use and manufacture of lead anchors and implantable devices. In addition, the invention is directed to lead anchors for implantable spinal cord stimulators, as well as the stimulators themselves and methods of use and manufacture of the lead anchors and spinal cord stimulators.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741, 892; and U.S. patent application Ser. Nos. 10/353,101, 10/503,281, 11/238,240; 11/319,291; 11/327,880; 11/375, 638; 11/393,991; and 11/396,309, all of which are incorporated by reference.

Figure 1:
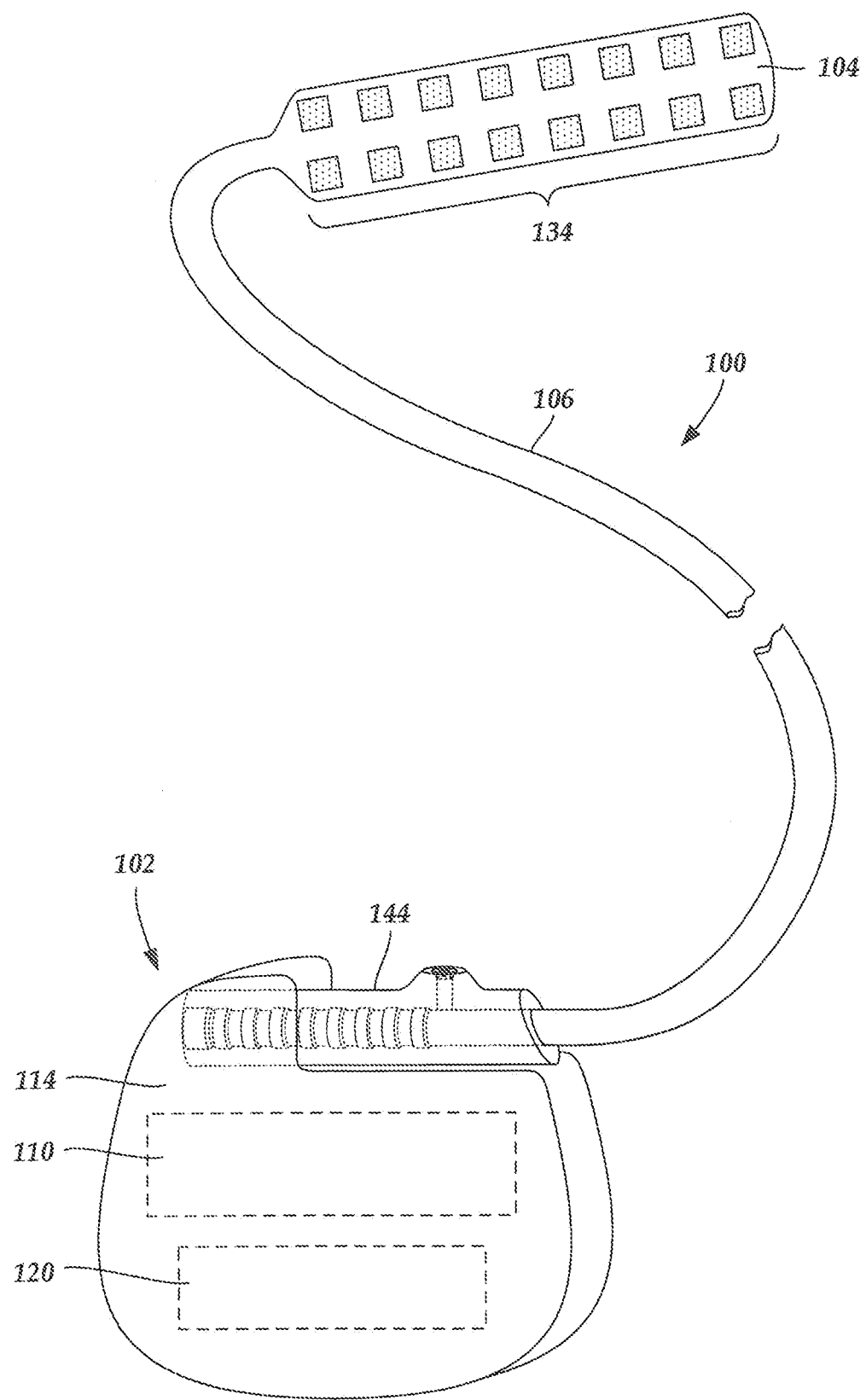
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104.

Figure 2:
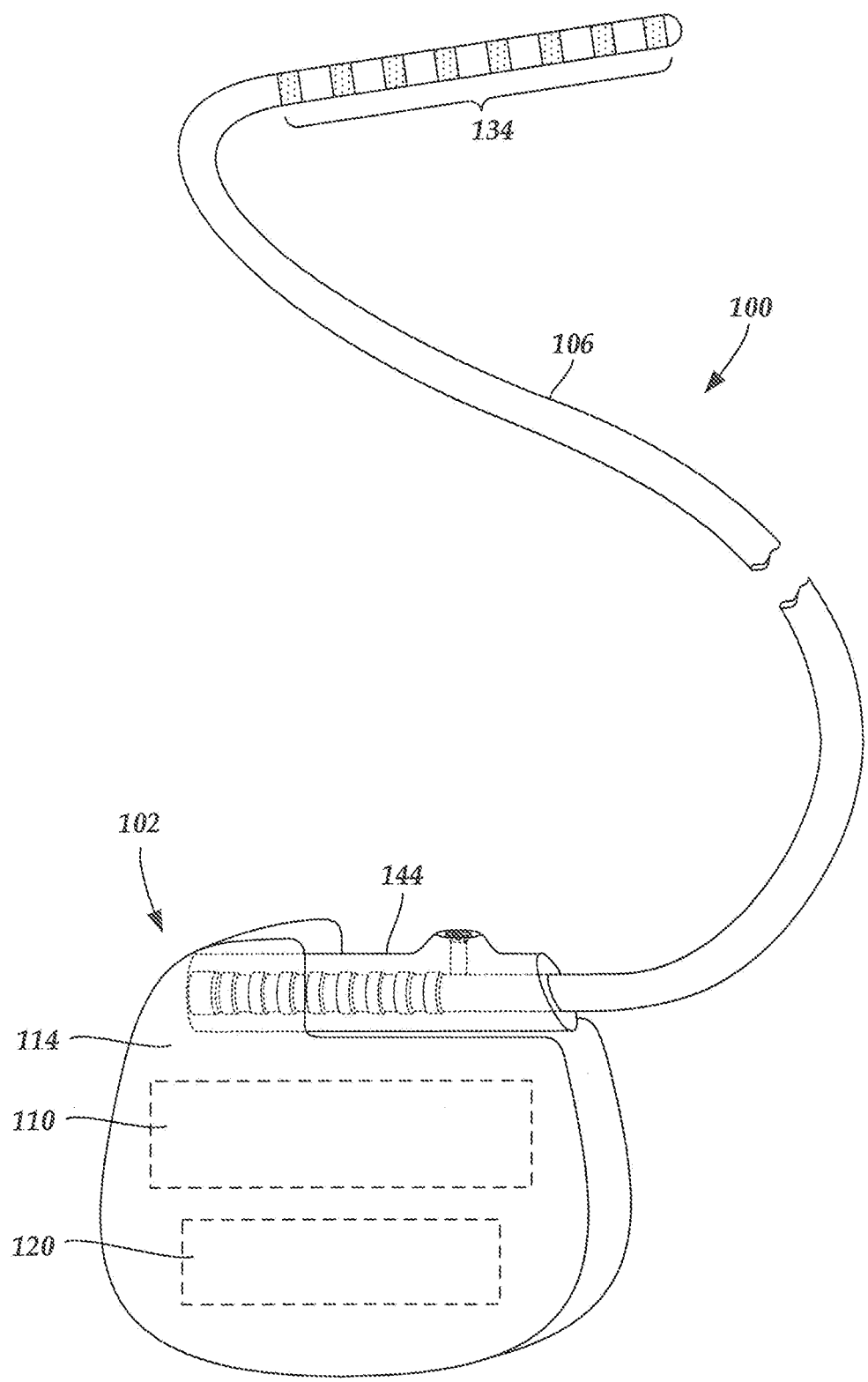
FIG. 2 is a schematic view of another embodiment of an electrical stimulation system, according to the invention.

The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via connector contacts on the control module 102 and terminals (e.g., 310 in FIGS. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone, epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIGS. 3A and 336 of FIG. 3B) are typically disposed at the proximal end of the one or more lead bodies 106 for connection to corresponding connector contacts (e.g., 314 in FIGS. 3A and 340 of FIG. 3B) in connectors (e.g., 144 in FIGS. 1-3A and 322 and 350 of FIG. 3B) disposed on, for example, the control module 102 (or to other devices, such as connector contacts on a lead extension, an operating room cable, or an adaptor). Conductive wires ("conductors") (not shown) extend from the terminals (e.g., 310 in FIGS. 3A and 336 of FIG. 3B) to the electrodes 134. Typically, one or more electrodes 134 are electrically coupled to a terminal (e.g., 310 in FIGS. 3A and 336 of FIG. 3B). In some embodiments, each terminal (e.g., 310 in FIGS. 3A and 336 of FIG. 3B) is only connected to one electrode 134. The conductors may be embedded in the non-conductive material of the lead or can be disposed in one or more lumens (not shown) extending along the lead. In some embodiments, there is an individual lumen for each conductor. In other embodiments, two or more conductors may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
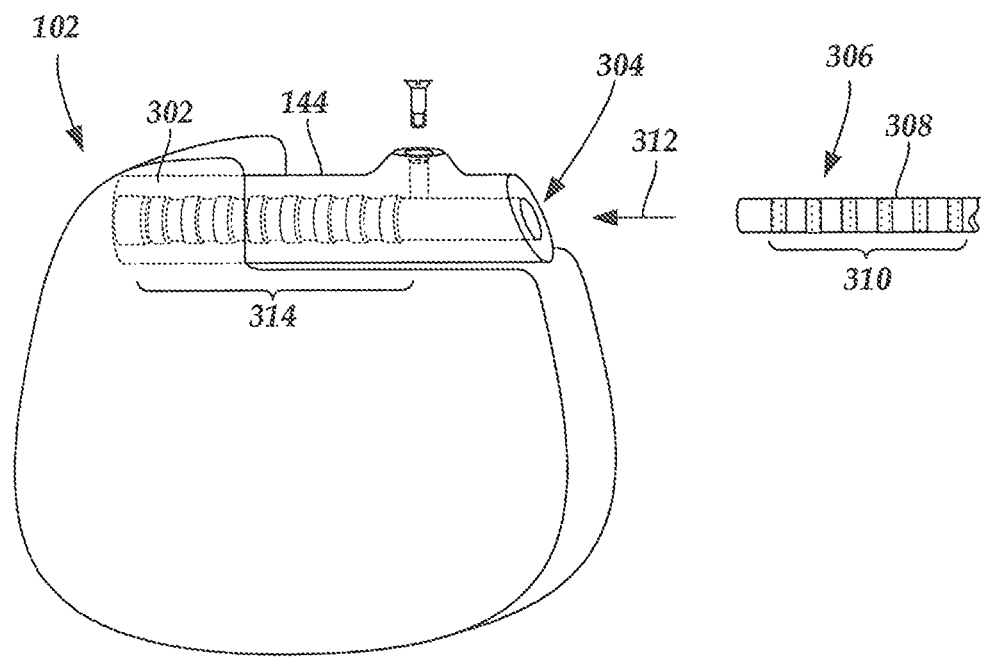
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of connector contacts 314 for each port 304. When the lead 308 is inserted into the port 304, the connector contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
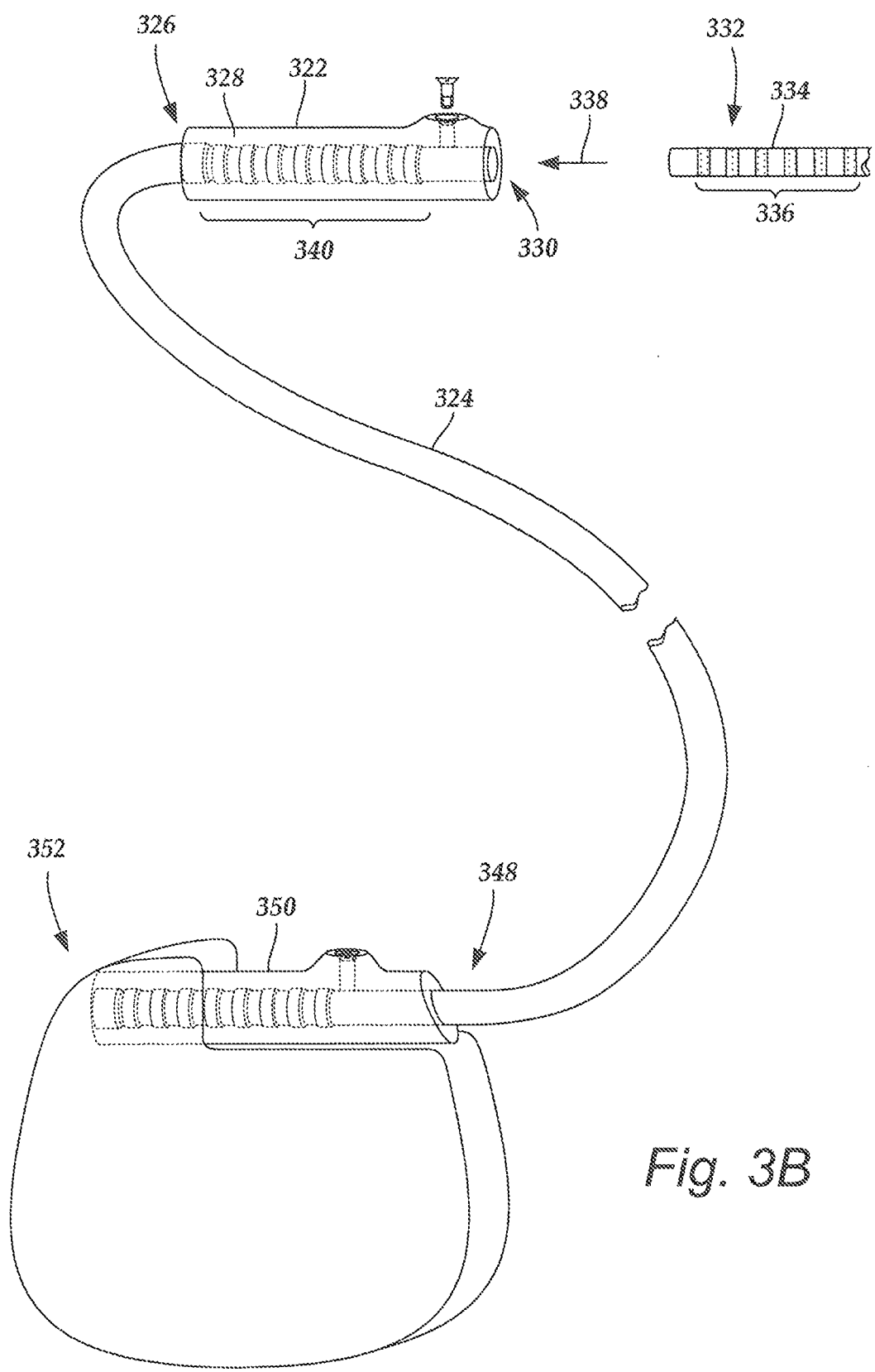
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of connector contacts 340. When the lead 334 is inserted into the port 330, the connector contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductors (not shown) that electrically couple the connector contacts 340 to a proximal end 348 of the lead extension 324 that is opposite to the distal end 326. In at least some embodiments, the conductors disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

A lead anchor can be used in an implantable device, such as an implantable spinal cord stimulator, to anchor a lead connecting a control module to an electrode array. The lead anchor includes a fastener, which may be tightened to hold the lead. In at least some embodiments, the lead anchor applies gentle compression to the lead to hold the lead in place.

Figure 4A:
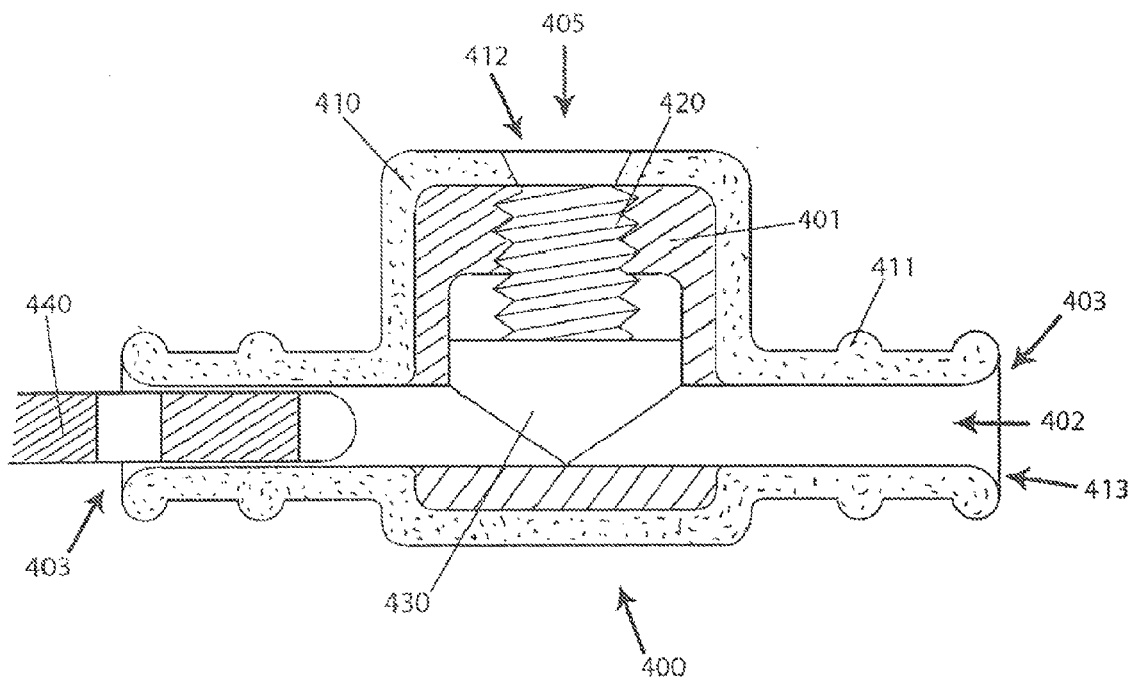
FIG. 4A is a schematic cross-sectional view of one embodiment of a torque lead anchor with a pressure plate according to the invention.

FIG. 4A is a schematic cross-sectional view of one embodiment of a torque lead anchor 400. As shown in FIG. 4A, the torque lead anchor 400 includes a body 401 and an exterior member 410. The body 401 may be made of a metal, such as titanium, nickel, aluminum, stainless steel, copper, gold, silver, platinum and alloys thereof or any other biocompatible metal, or a rigid plastic or polymer material. The exterior member 410 may be formed of any biocompatible material such as plastics and polymers including, but not limited to, silicone, polyvinyl chloride, fluoropolymers, polyurethane, polycarbonate, acrylic compounds, thermoplastic polyesters, polypropylene, low-density polyethylenes, and other thermoplastic elastomers. In some embodiments, the exterior member 410 is made of silicone. In some embodiments, the exterior member and the body are made of the same material. In some embodiments, the exterior member and the body are unitary.

Furthermore, it may be useful for any or all parts of the lead anchor to be made of a material that is radiopaque, so that it is visible under fluoroscopy or other forms of x-ray diagnosis. In some embodiments, the body or the exterior member is radiopaque so as to allow the lead anchor to be readily identified under fluoroscopy or other forms of x-ray diagnosis. The lead itself may also be radiopaque.

The body 401 contains a lead lumen 402 through which a lead 440 may pass. The lead lumen 402 has a first opening 403 and a second opening 404 for insertion of the lead. The lead lumen 402 may have a cross-section that is substantially circular as it extends from the first opening 403 to the second opening 404. It is contemplated that the lead lumen 402 may also have a cross-section in the shape of a triangle, a square, an ovoid, or any other suitable shape that is large enough to house the lead 440. In some embodiments the lead lumen 402 may be defined so that the lead 440 passes along a straight path through the center of the body 401. Conversely the lead lumen 402 may be defined so that the lead 440 passes at an angled path through the body 401. In some embodiments, the lead lumen 402 is defined as a curved path through the body 401. In some embodiments, the body 401 contains more than one lead lumen so that the lead anchor 400 is able to house more than one lead. The opening may be a friction fit with the lead or can be large enough to allow the lead to pass through freely. In some embodiments, the lead lumen 402 is formed of a tapped and reamed through lumen. As seen in FIG. 4D, the lead lumen 402 may also include ridges 450, which may be concentric, for better engagement with the lead 440. The lead lumen 402 may alternatively define an interior thread or another pattern for better engagement with the lead 440.

The body 401 further defines a transverse lumen 405 for accepting a fastener 420. The transverse lumen 405 may have a cross-section that is substantially circular. In other embodiments, the body 401 defines a transverse lumen 405 with a cross-section in the shape of a triangle, a square, an ovoid, or any other suitable shape that is capable of housing the fastener 420. In some embodiments, the transverse lumen 405 is positioned perpendicular to the central axis of the lead lumen 402. In other embodiments, the transverse lumen 405 may be defined so that the fastener 420 engages a lead 440 within the lead lumen 402 at a 15, 30, or 45 degree angle or any other suitable angle with respect to the central axis of the lumen. In some embodiments, the transverse lumen 405 intersects the lead lumen 402 and extends through it so that a cross-shaped void is formed through the body 401. In at least some embodiments, the transverse lumen 405 merges with the lead lumen 402 but does not extend through it, so that the cross-section of the body 401 defines a T-shaped bore. In at least some embodiments, the two lumens intersect with a sleeve or a plate disposed between the two (see, e.g., FIGS. 6 and 7). In embodiments with multiple lead lumens, the body 401 may define more than one transverse lumen for accepting a plurality of fasteners. Additionally, the body 401 may define a transverse lumen 405 having a thread, groove, crease, channel, duct or rib for facilitating or accepting the fastener 420.

The fastener 420 may be, for example, a pin, clamp, latch, lug, nail, bolt, dowel, rod, rivet, screw or any combination thereof or any other suitable item for engaging and anchoring the lead. The fastener 420 may engage or couple to the lead anchor 400 by any method such as, for example, tightening, screwing or pushing. In some embodiments, the fastener 420 is a set screw with a thread to be received by the transverse lumen 405 of the body 401. The set screw may be tightened through the use of a torque limiting tool 1100 (see FIG. 11), which will be described in greater detail below. As the fastener 420 engages the body 401 through the transverse lumen 405, it is brought closer to the lead lumen 402.

Figure 5:
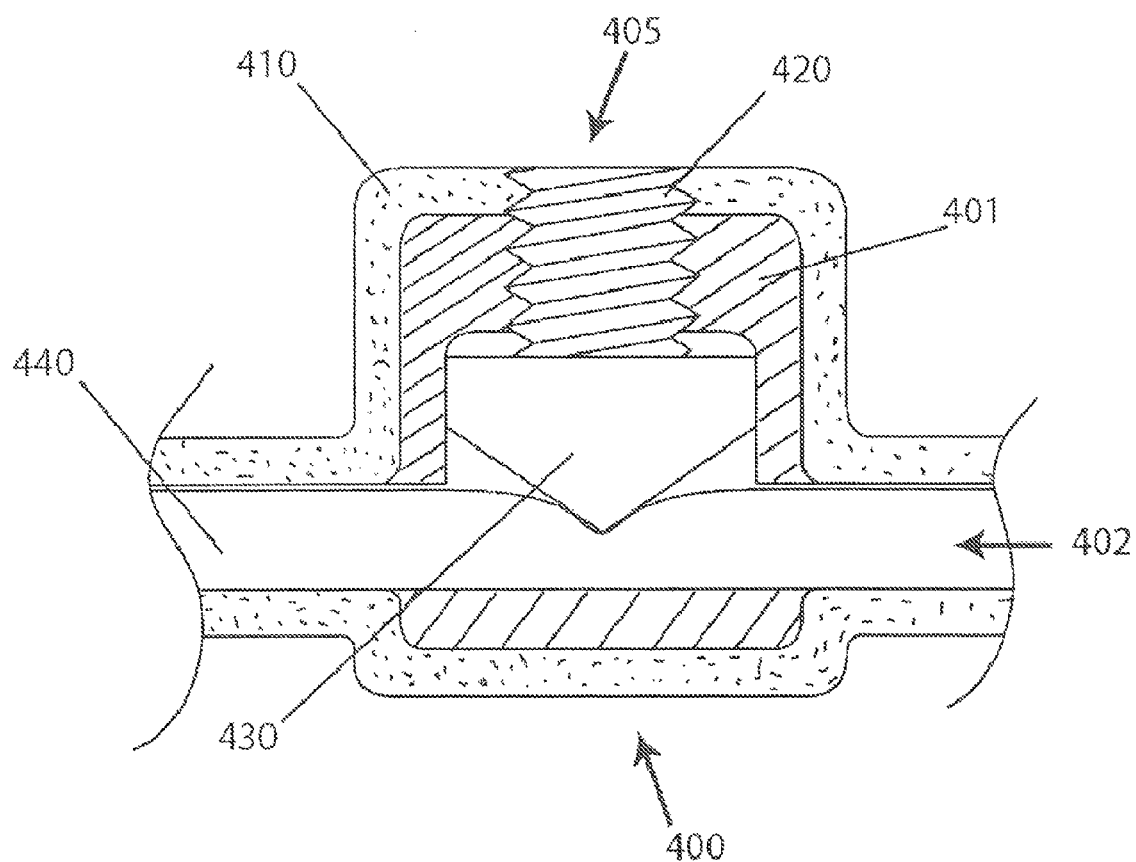
FIG. 5 is a schematic cross-sectional view of the torque lead anchor of FIG. 4A after a lead has been inserted in the lead anchor according to the invention.

In some embodiments, the fastener 420 engages a pressure plate 430 positioned within the transverse lumen 405. As the fastener 420 is tightened, the pressure plate 430 is moved within the body 401 to obstruct the lead lumen 402. When a lead 440 is placed within the lead lumen 402 and the fastener 420 is tightened, the pressure plate 430 closes down on the lead to keep it in place. As seen in FIGS. 4A and 5, in some embodiments, the cross section of the pressure plate 430 may be in the shape of a triangle. Alternatively, the cross-section of the pressure plate 430 may be in the shape of a circle, an ovoid, a rectangle, or any other suitable shape. In at least some embodiments, the lead is deformed when the pressure plate 430 is brought into position. In some embodiments, the deformation is slight (e.g., no more than 5% or 10% of the thickness of the lead). In other embodiments, the deformation is more significant (e.g., at least 10% or 25% of the thickness of the lead). The pressure plate 430 may be made of any suitable material, such as, for example, a metal such as titanium, nickel, aluminum, stainless steel, copper, gold, silver, platinum and alloys thereof, or a plastic, rubber or polymer such as polyurethane. In other embodiments (not shown), the fastener 420 directly contacts the lead 440 to lock it in position within the lead anchor 400.

In at least some embodiments, surrounding the body 401, an exterior member 410 may be formed of any suitable biocompatible material. The exterior member 410 may partially or completely surround the body 401. In some embodiments, the exterior member 410 forms a skin around the body 401.

As seen in FIG. 4D, the exterior member 410 may also include a septum 451. The septum 451 may comprise silicone. It will be understood that the septum 451 may also be formed of any elastic, biocompatible material including, but not limited to, those suitable for the exterior member 410. In some embodiments, the septum 451 and the exterior member 410 are unitary and formed of the same material. In at least some other embodiments, the septum 451 is a separate member that is attached, glued, fixed, or otherwise coupled to the exterior member 410. The septum 451 may be disposed on the exterior member 410 over the transverse lumen 405 to prevent the set screw from being disengaged from the torque lead anchor 400. In some embodiments, the septum 451 includes a slit 452, or opening to allow a tool to reach the fastener 420. The slit 452 may be large enough to accept the tool, but too small for the fastener 420 to disengage from the torque lock anchor 400.

In at least some embodiments, the exterior member 410 further defines at least one suture element 411. The suture element 411 may be a groove, stub, ridge, eyelet, opening or bore or any other suitable arrangement for suturing the torque lead anchor 400 to the fascia, ligament or other tissue or body structure. The suture element 411 may be positioned anywhere around the circumference of the exterior member 410. In some embodiments, a plurality of suture elements are disposed on the exterior member 410. The exterior member 410 may also define an exterior transverse aperture 412 for receiving the fastener 420 and an exterior lead aperture 413 for receiving the lead.

Figure 4B:
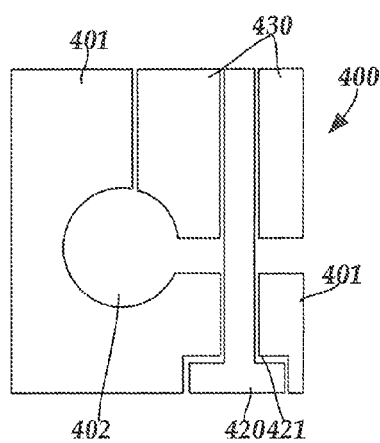
FIG. 4B is a schematic cross-sectional view of another embodiment of a torque lead anchor with a pressure plate according to the invention.
Figure 4C:
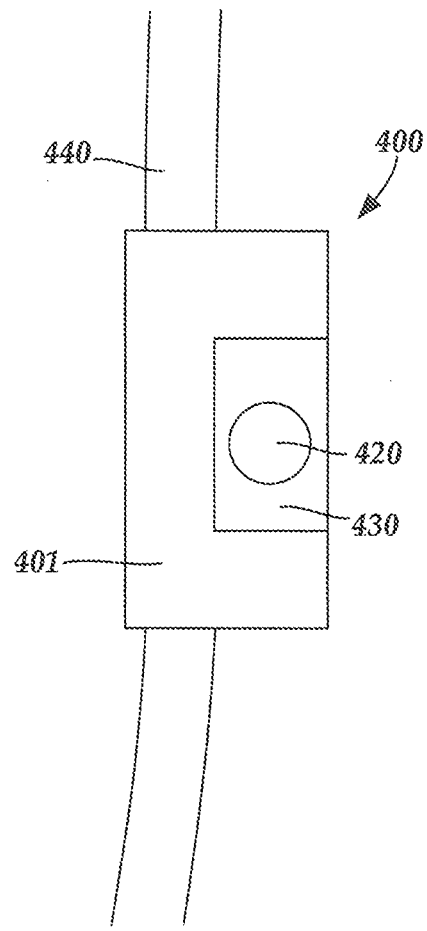
FIG. 4C is a schematic side view of the torque lead anchor of FIG. 4B, according to the invention.
Figure 4D:
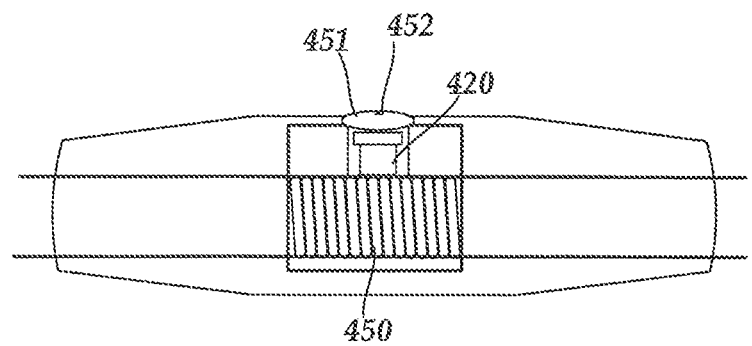
FIG. 4D is a schematic cross-sectional view of another embodiment of a torque lead anchor with a septum, according to the invention.

FIG. 4B is a schematic cross-sectional view of another embodiment of a torque lead anchor with a pressure plate. The torque lead anchor of FIG. 4B includes a body 401 similar to that of FIG. 4A. The body defines a lead lumen 402 and a fastening lumen 421. The torque lead anchor 400 also includes a pressure plate 430. In some embodiments, as the fastener 420 is tightened, the pressure plate is drawn in contact with the lead (not shown) disposed within the lead lumen 402. Thus, when the fastener 420 is tightened, the pressure plate 430 is drawn toward to the body 401, the cross-sectional area of the lead lumen is reduced and the lead is secured. As an example, the fastener 420 and the interior of the fastening lumen 421 of the pressure plate 430 are threaded so that the tightening the fastener 420 draws the pressure plate 430 in contact with the lead. FIG. 4C is a schematic top view of the torque lead anchor 400 of FIG. 4B. As can be appreciated from FIG. 4C, the torque lead anchor 400 may be formed with a lower profile so that the lead anchor 400 does not excessively project from the surface of the tissue.

FIG. 5 is a schematic cross-sectional view of the torque lead anchor 400 of FIG. 4A after a lead 440 has been inserted in the lead anchor. As can be appreciated from FIG. 5, as the fastener 420 is tightened, the pressure plate 430 is brought in contact with the lead 440 within the lead lumen 402. When the fastener 420 is completely tightened, the lead is locked in place within the lead anchor. In some embodiments, the lead 440 is partially deformed when locked in place.

Figure 6:
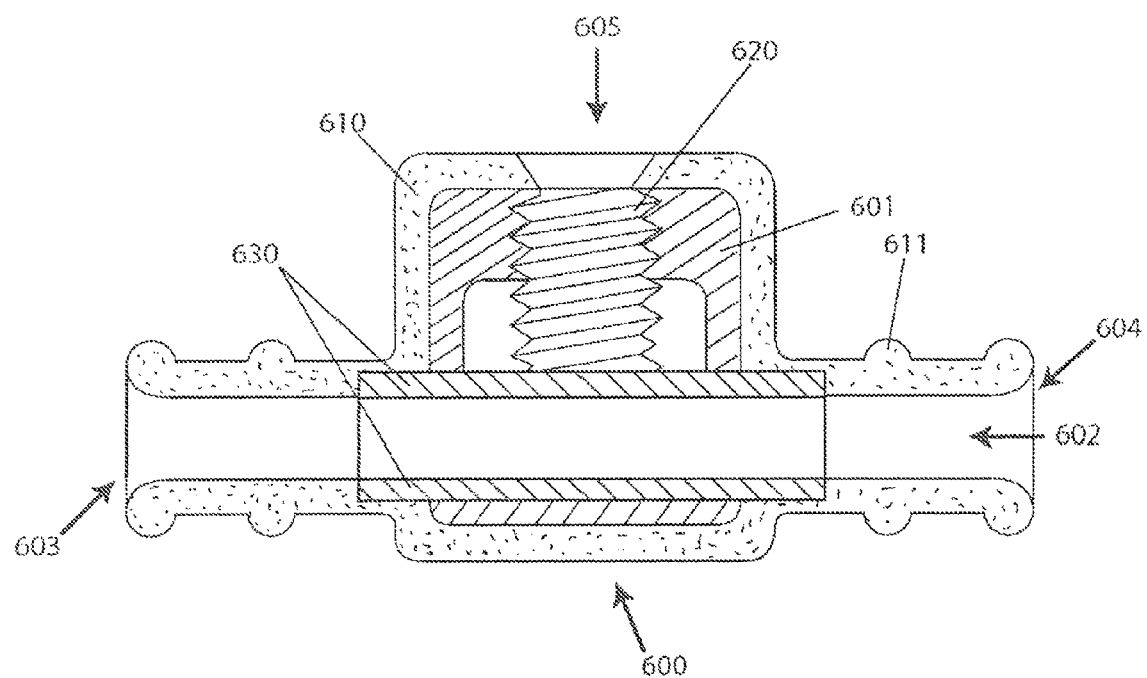
FIG. 6 is a schematic cross-sectional view of one embodiment of a torque lead anchor with a sleeve according to the invention.

FIG. 6 is a schematic cross-sectional view of another embodiment of a torque lead anchor 600 with a sleeve. As shown in FIG. 6, the torque lead anchor 600 comprises a body 601 and an exterior member 610. The body 601 further contains a lead lumen 602 through which a lead may pass. The lead lumen 602 has a first opening 603 and a second opening 604 for insertion of the lead. The body 601 further defines a transverse lumen 605 for accepting a fastener 620. Surrounding the body 601, an exterior member 610 may be formed of a biocompatible material. The exterior member 610 further defines a suture element 611.

As depicted in FIG. 6, in some embodiments, the fastener 620 engages a sleeve 630 positioned within the lead lumen 602. The sleeve 630 may be a substantially hollow cylinder or sheath, and may be made of any suitable material, for example, a metal such as titanium, nickel, aluminum, stainless steel, copper, gold, silver, platinum and alloys thereof, or a plastic, rubber or polymer such as polyurethane. In other embodiments, the fastener 620 directly contacts the lead to lock it in position within the lead anchor. In some embodiments the sleeve 630 is disposed within the body 601 and receives the lead when the lead is passed through the first opening 603 of the lead lumen 602. In another embodiment, the sleeve 630 is removable and is placed around the lead before it is inserted into the lead anchor 600. In some embodiments, the sleeve is deformable when the fastener is tightened. The deformation of the sleeve may be slight (e.g., no more than 5% or 10% of the thickness of the sleeve) or more significant (e.g., at least 10% or 25% of the thickness of the sleeve).

Figure 7:
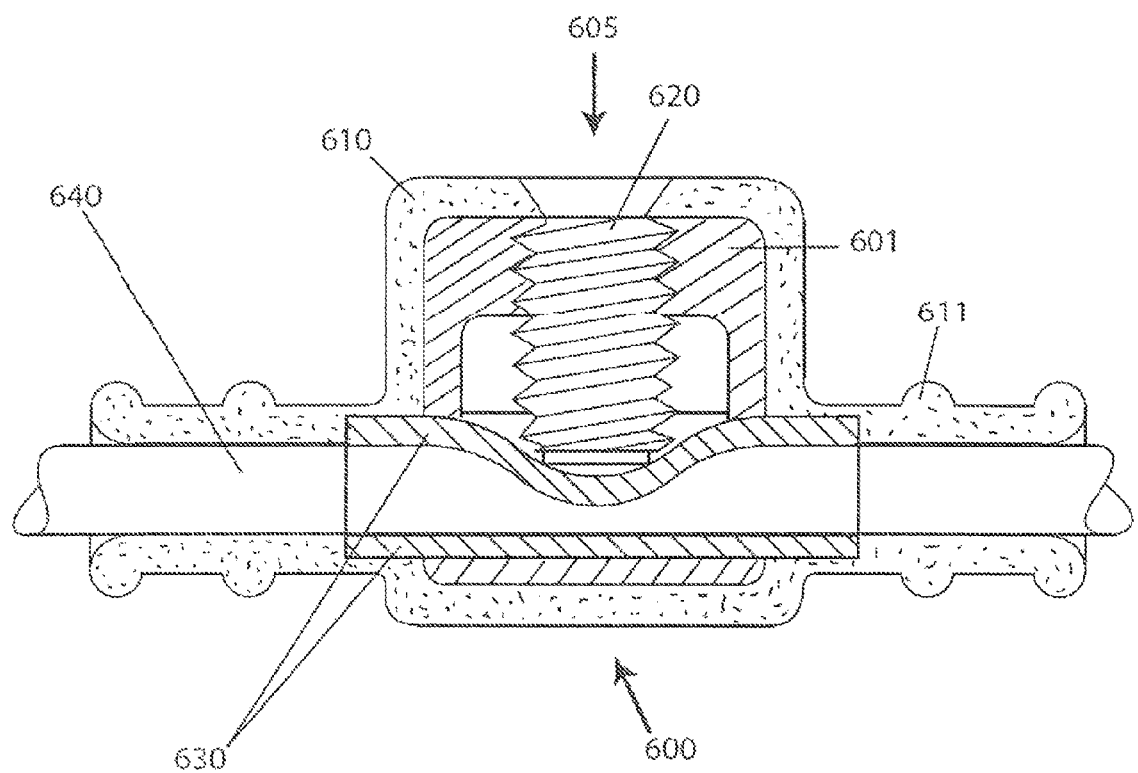
FIG. 7 is a schematic cross-sectional view of the torque lead anchor of FIG. 6 after a lead has been inserted in the lead anchor according to the invention.
Figure 8A:
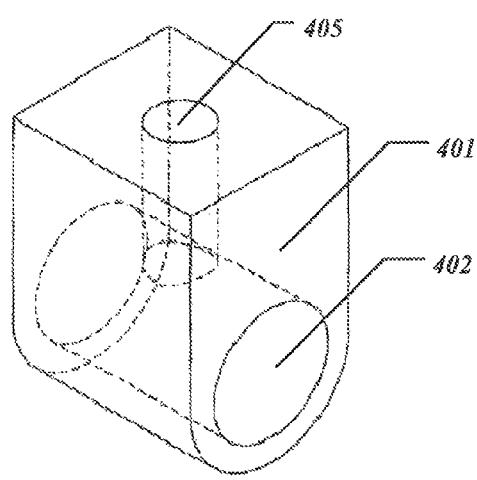
FIG. 8A is a schematic perspective view of a portion of another embodiment of a lead anchor according to the invention.
Figure 8B:
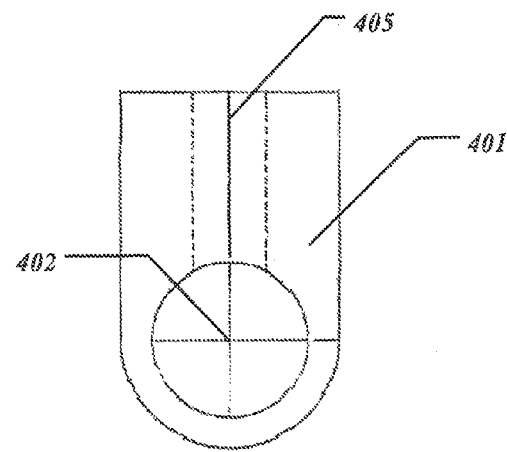
FIG. 8B is a schematic side view of the portion of the lead anchor of FIG. 8A according to the invention.
Figure 8C:
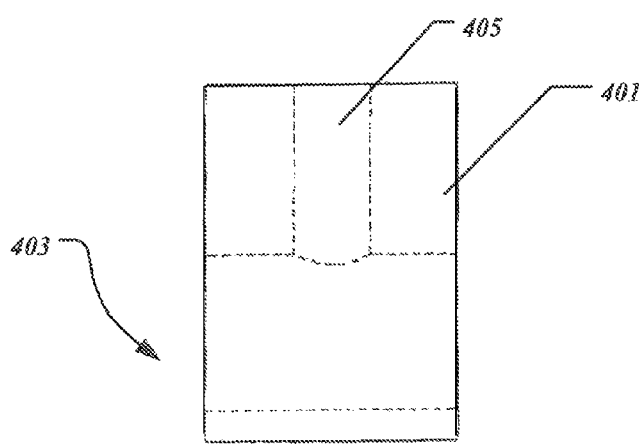
FIG. 8C is a schematic front view of the portion of the lead anchor of FIG. 8A according to the invention.
Figure 8D:
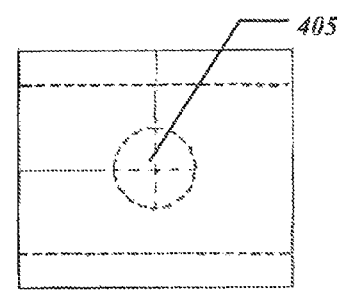
FIG. 8D is a schematic top view of the portion of the lead anchor of FIG. 8A according to the invention.

FIG. 7 is a schematic cross-sectional view of the torque lead anchor 600 of FIG. 6 after a lead 640 has been inserted in the lead anchor. As the fastener 620 is tightened, the sleeve 630 is deformed and obstructs the lead lumen. When a lead 640 is placed within the lead lumen and the fastener 620 is tightened, the sleeve 630 closes down on the lead to keep it in place. In at least some embodiments, the lead 640 is partially deformed when the sleeve 630 is acted upon by the fastener.

FIGS. 8A-8D are schematic views of a portion of another embodiment of a lead anchor. As illustrated, the body 401 contains a lead lumen 402 for receiving a lead and a transverse lumen 405 for receiving a fastener 420. The lead lumen 402 may have a radius smaller, equal to, or greater than the radius of the transverse lumen 405. In at least some embodiments, the height of the body 401 may be between 0.200 and 0.600 inches (0.508 to 1.52 cm) or between 0.200 and 0.400 inches (0.508 to 1.02 cm). In at least some embodiments, the length of the body 401 may be between 0.200 and 0.400 inches (0.508 to 1.02 cm) or between 0.100 and 0.300 inches (0.254 to 0.762 cm). In at least some embodiments, the width of the body 401 may be between 0.100 and 0.300 inches (0.254 to 0.762 cm) or between 0.200 and 0.500 inches (0.508 to 1.27 cm).

FIGS. 9A-9D are schematic views of a portion of one embodiment of a lead anchor. As can be appreciated from FIG. 9A, the exterior member 410 contains an exterior transverse aperture 901 for receiving a fastener and an exterior lead aperture 902 for receiving a lead. Thus a fastener (not shown) is disposed in the exterior transverse aperture 901 and a lead (not shown) is inserted through the exterior lead aperture 902 and into the lead lumen of the body. As can be appreciated from FIGS. 9A, 9B and 9C, the lead anchor may also contain one or more suture tabs 904 extending from the exterior member 410 and suture eyelets 903 formed in the suture tabs for suturing the lead anchor to the fascia or ligament. In at least some embodiments, the sutures are wrapped or tied around the anchor using the v-shaped portions of the exterior member.

Figure 9A:
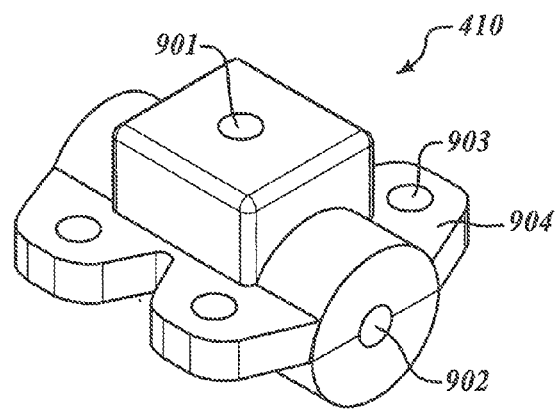
FIG. 9A is a schematic perspective view of a portion of another embodiment of a lead anchor according to the invention.
Figure 9B:
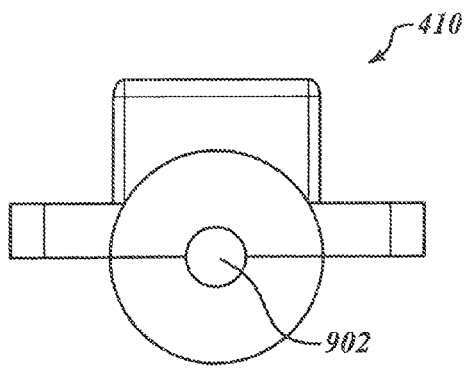
FIG. 9B is a schematic side view of the portion of the lead anchor of FIG. 9A according to the invention.
Figure 9C:
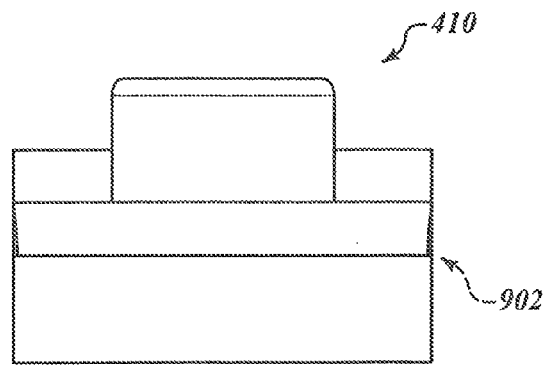
FIG. 9C is a schematic front view of the portion of the lead anchor of FIG. 9A according to the invention.
Figure 9D:
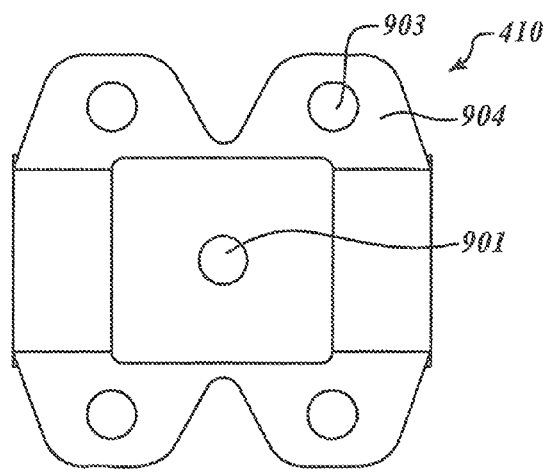
FIG. 9D is a schematic top view of the portion of the lead anchor of FIG. 9A according to the invention.
Figure 10:
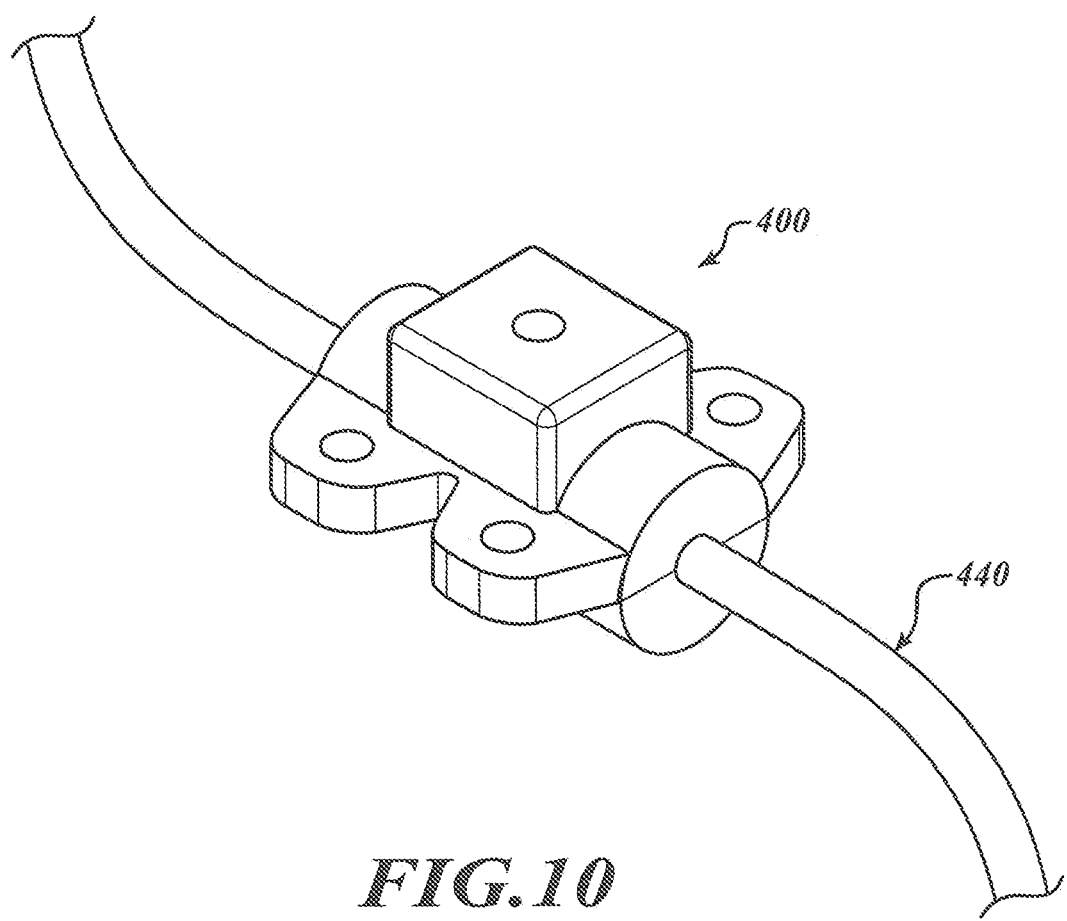
FIG. 10 is a schematic perspective view of the lead anchor of FIG. 9A attached to a lead according to the invention.

FIG. 10 is a schematic perspective view of the lead anchor 400 of FIG. 9A attached to a lead 440. Initially, a lead 440 is placed in position to achieve the desired parathesia at the chosen site of stimulation. In at least some embodiments, the lead is inserted through the exterior lead aperture and into the lead lumen 402 of the body 401. The lead anchor 400 is slid along the length of the lead until it is in the desired position for anchoring to the ligament or fascia. In other embodiments, the body 401, the exterior member 410, or both may be formed of two complementary members that, when joined around a lead 440, form the lead anchor. Thus, no sliding of the lead is necessary. Each of the two complementary members maybe joined together through clasps, buckles, fasteners or by any other suitable arrangement. After the lead has been positioned as desired a fastener is tightened so that the lead 440 is locked in place within the lead anchor 400.

Figure 11:
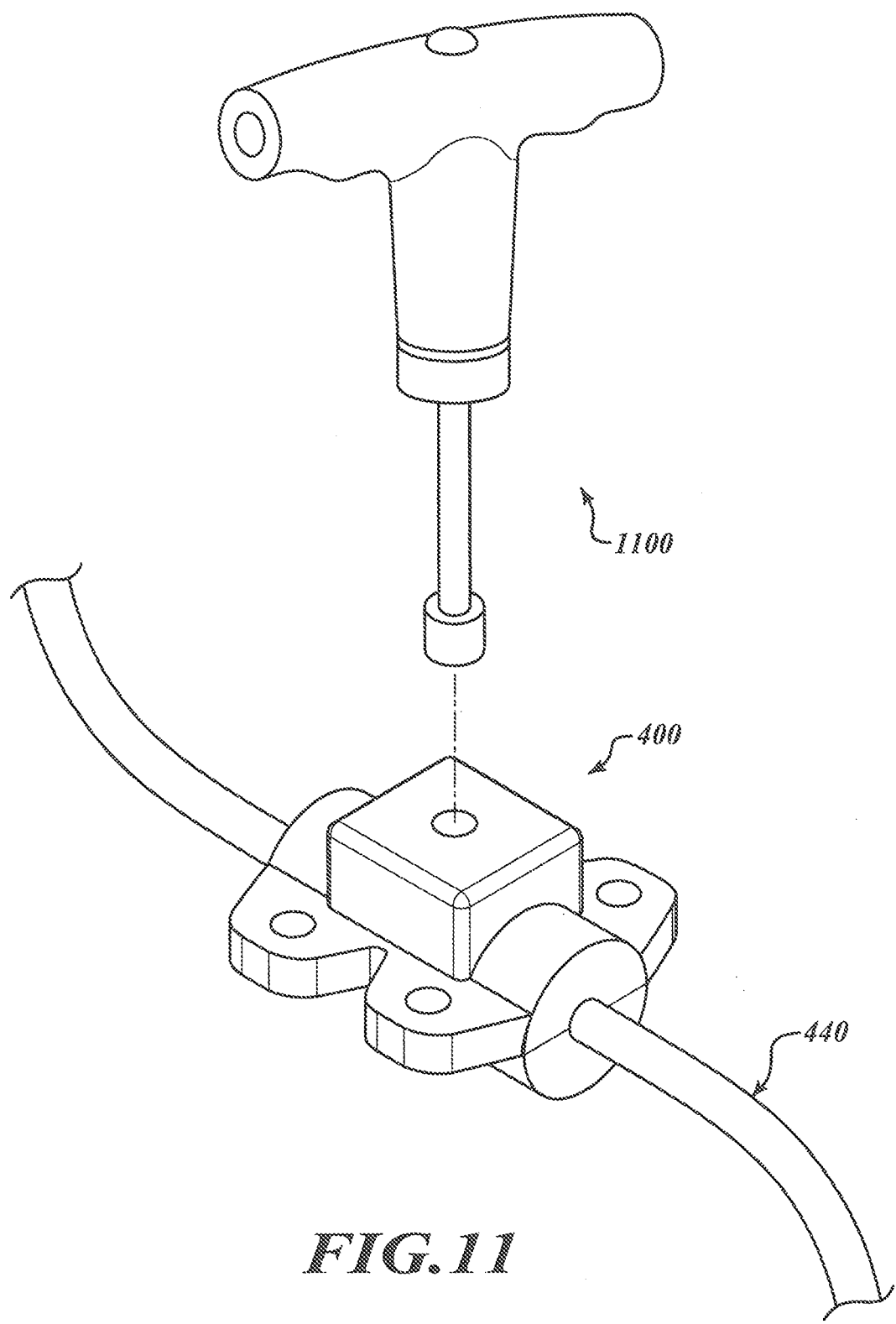
FIG. 11 is a schematic perspective view of the lead anchor of FIG. 9A and a tool according the invention.

FIG. 11 is a schematic perspective view of the lead anchor 400 of FIG. 9A and a tool 1100. The tool 1100 may be a screwdriver, wrench, pliers, or drill or any other suitable tool useful for setting, fixing, screwing, tightening, fastening or fitting a fastener with the lead anchor 400. In at least some embodiments, the tool 1100 is a torque limiting tool set to a certain threshold above which it will no longer tighten the fastener. With this method, over-tightening of the fastener is avoided and the lead can be protected from possible damage due to overtightening the fastener. For example, the torque limiting tool may be configured to limit the number of revolutions or the depth to which a fastener may be advanced.

Figure 13A:
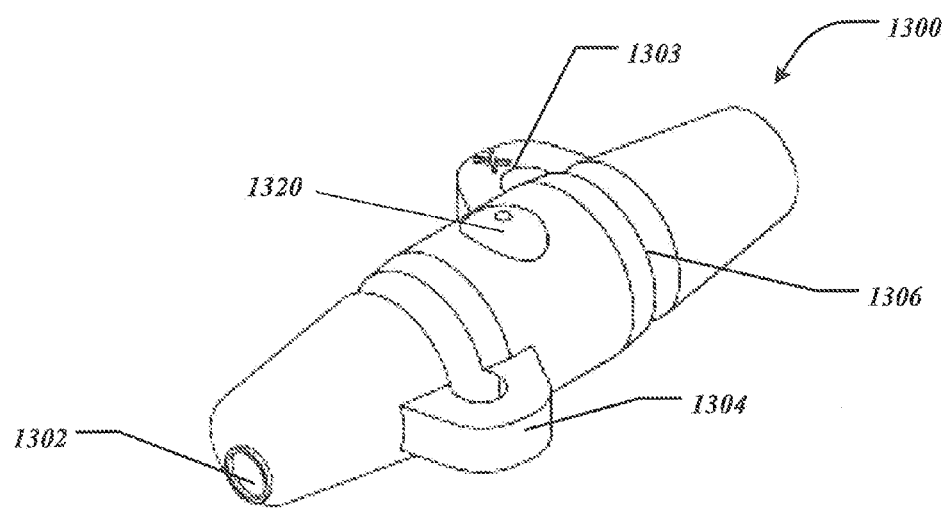
FIG. 13A is a schematic perspective view of another embodiment of a lead anchor, according to the invention.
Figure 13B:
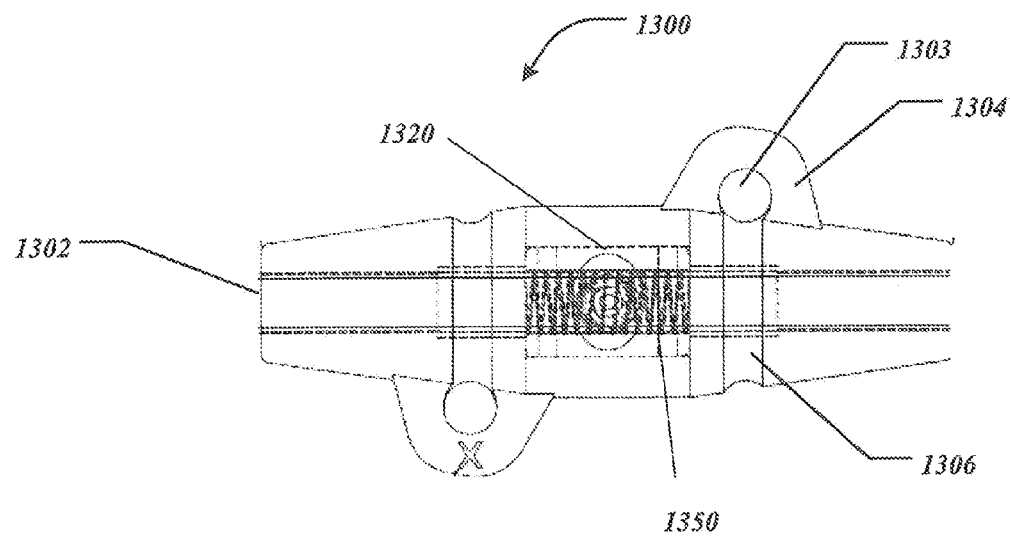
FIG. 13B is a schematic bottom view of the lead anchor of FIG. 13A, according to the invention.
Figure 13C:
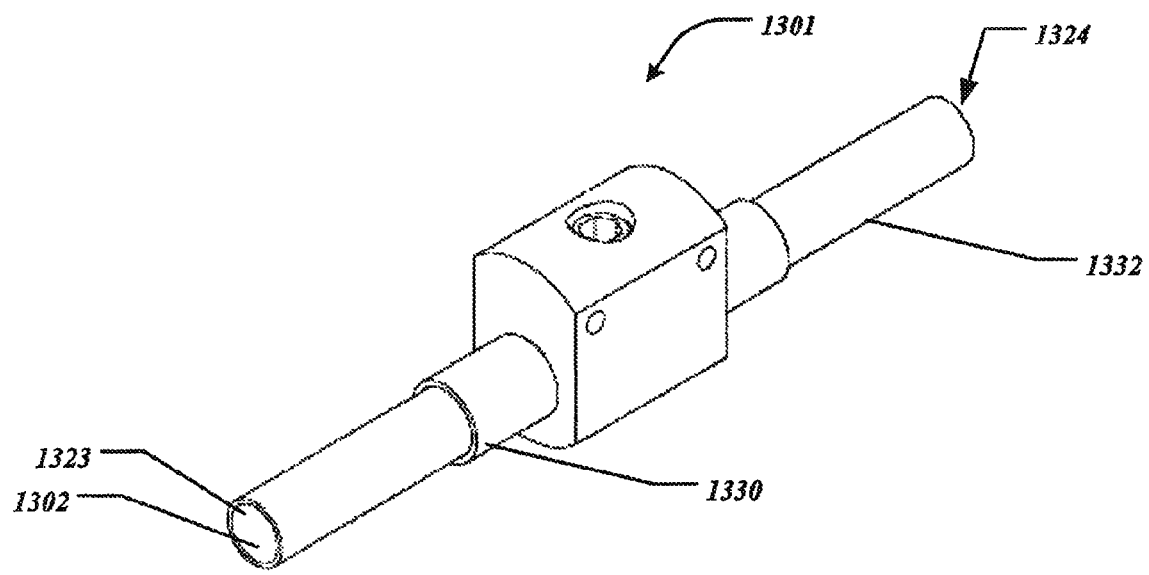
FIG. 13C is a schematic perspective view of a body of the lead anchor of FIG. 13A, according to the invention.
Figure 13D:
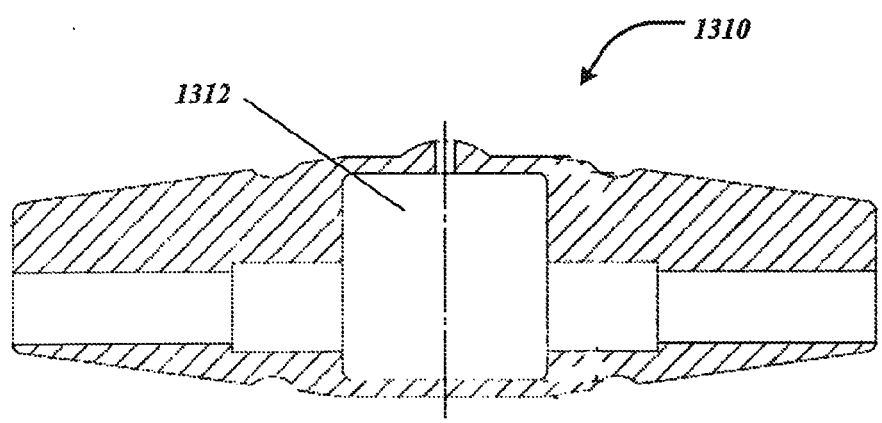
FIG. 13D is a schematic cross-sectional view of an exterior member of the lead anchor of FIG. 13A, according to the invention.

FIGS. 13A to 13D are schematic views of another embodiment of a lead anchor. FIGS. 13A and 13B illustrate the assembled lead anchor 1300. FIG. 13C illustrates a body 1301 of the lead anchor and FIG. 13D is a cross-sectional view of an exterior member 1310 that fits around the body 1301 to form the lead anchor. As can be appreciated from FIG. 13A, the lead anchor 1300 contains an exterior transverse aperture 1305 (FIG. 13C) for receiving a fastener 1320 and an exterior lead aperture 1302 for receiving a lead. Thus a fastener is disposed in the exterior transverse aperture 1305 (FIG. 13C) and a lead (not shown) is inserted through the exterior lead aperture 1302 and into the lead lumen of the body.

As can be appreciated from FIGS. 13A and 13B, the lead anchor 1300 may also contain one or more suture tabs 1304 extending from the lead anchor 1300 (e.g., from the exterior member 1310) and suture eyelets 1303 in the suture tabs for suturing the lead anchor to the fascia or ligament. The suture tabs 1304 can be placed in any suitable arrangement around the lead anchor. For example, one or more suture tabs 1304 can extend from opposite sides of the lead anchor (see, e.g., FIGS. 13A and 9A). Suture tabs extending from opposite sides of the lead anchor can be arranged in any manner including, but not limited to, directly across from each other (see, e.g., FIG. 9A) or in a staggered arrangement (see, e.g., FIG. 13A), for example, with one suture tab extending from a distal region of one side of the lead anchor and another suture tab extending from a proximal region of the opposing side of the lead anchor as illustrated in FIGS. 13A and 13B. The exterior member 1310 may also include one or more suture channels 1306 within which a suture can be wrapped around the lead anchor 1300. It will be understood that suture tabs, suture eyelets, and suture channels can be used with any of the lead anchor embodiments described herein.

As shown in FIGS. 13C and 13D, the torque lead anchor 1300 may include a body 1301 and an exterior member 1310. The body 1301 may be made of a metal, such as titanium, nickel, aluminum, stainless steel, copper, gold, silver, platinum and alloys thereof or any other biocompatible metal, or a rigid plastic or polymer material. The exterior member 1310 includes a space 1312 for receiving the body 1301. The exterior member 1310 may be formed of any biocompatible material such as plastics and polymers including, but not limited to, silicone, polyvinyl chloride, fluoropolymers, polyurethane, polycarbonate, acrylic compounds, thermoplastic polyesters, polypropylene, low-density polyethylenes, and other thermoplastic elastomers. In at least some embodiments, the exterior member 1310 is made of silicone.

The body 1301 may contain a lead tube 1332 with a lead lumen 1302 through which a lead may pass. The lead tube 1332 has a first opening 1323 and a second opening 1324 for insertion of the lead. The lead tube 1332 may also include ridges 1350 (FIG. 3B), which may be concentric or spiraling, for better engagement with the lead. The lead tube 1332 may alternatively define an interior thread or another pattern for better engagement with the lead. The lead tube 1332 may be made of a metal, such as titanium, nickel, aluminum, stainless steel, copper, gold, silver, platinum and alloys thereof or any other biocompatible metal, or a rigid plastic or polymer material.

Optionally, the body 1301 includes a sleeve 1330. The sleeve 1330 may be a substantially hollow cylinder or sheath, and may be made of any suitable material, for example, a metal such as titanium, nickel, aluminum, stainless steel, copper, gold, silver, platinum and alloys thereof, or a plastic, rubber or polymer such as polyurethane. In operation, when the fastener 1320 is fastened to retain the lead within the lead anchor, the fastener engages the sleeve 1330 positioned within the lead lumen 1302. The sleeve 1330, in turn, engages the lead.

Figure 12:
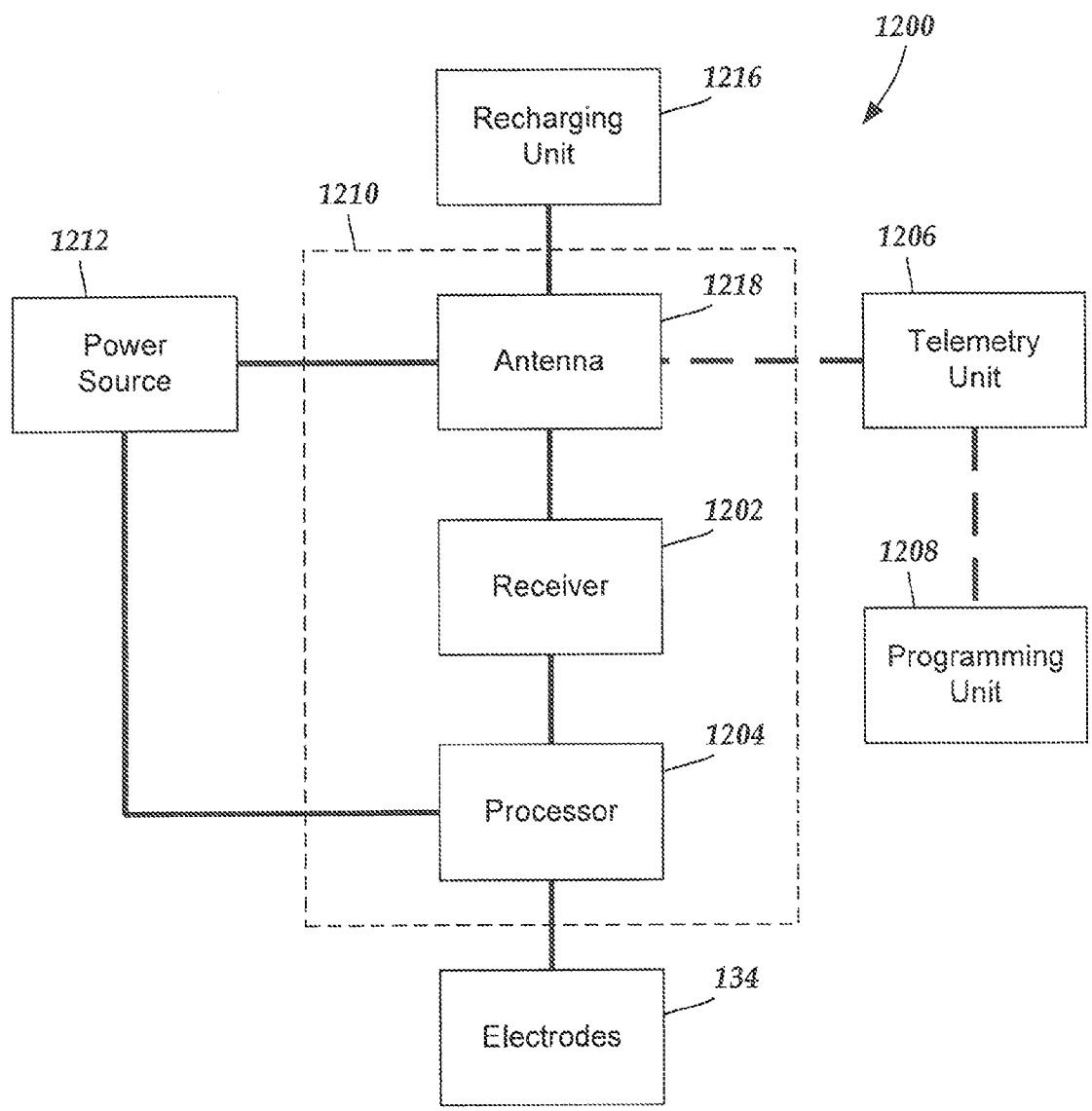
FIG. 12 is a schematic overview of one embodiment of components of an electrical stimulation system, including an electronic subassembly disposed within a control module, according to the invention.

FIG. 12 is a schematic overview of one embodiment of components of an electrical stimulation system 1200 including an electronic subassembly 1210 disposed within a control module. It will be understood that the electrical stimulation system can include more, fewer, or different components and can have a variety of different configurations including those configurations disclosed in the stimulator references cited herein.

Some of the components (for example, power source 1212, antenna 1218, receiver 1202, and processor 1204) of the electrical stimulation system can be positioned on one or more circuit boards or similar carriers within a sealed housing of an implantable pulse generator, if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1218 or a secondary antenna. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 may select which electrode(s) are cathodes and which electrode(s) are anodes. In some embodiments, the processor 1204 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by a programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and receiver 1202 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include an antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor, comprising:
 a body defining a lead lumen having a first opening and a second opening through which a lead can pass through the body and extend beyond the first and second openings outside the body such that the body is configured and arranged to slide along the lead, the body further defining a transverse lumen that intersects the lead lumen;
 a deformable sleeve at least partially disposed within the body and within the lead lumen, the sleeve extending out of at least one of the first opening or the second opening of the body and configured and arranged to receive a portion of the lead and slide along the lead;

a separate exterior member surrounding and forming a skin around the body so that the body is entirely disposed within the exterior member, the exterior member being formed of a biocompatible material;

a fastener for anchoring the lead to the body through the transverse lumen by engaging the sleeve to deform the sleeve to close down on a portion of the lead to anchor the lead in the lead anchor, wherein the fastener is a screw and the transverse lumen is configured and arranged to receive the fastener and the transverse lumen is accessible by a tool through a transverse opening in the exterior member to engage the fastener and tighten or loosen the fastener so that the fastener engages or disengages the sleeve; and at least two suture tabs extending from the exterior member and configured and arranged for receiving a suture to suture the lead anchor to patient tissue.

2. The lead anchor of claim 1, wherein the at least two suture tabs comprises exactly two suture tabs.

3. The lead anchor of claim 2, wherein the two suture tabs extend from opposite sides of the exterior member.

4. The lead anchor of claim 3, wherein the two suture tabs extend from opposite sides of the exterior member in a staggered arrangement.

5. The lead anchor of claim 1, wherein each of the at least two suture tabs comprises at least one suture opening.

6. The lead anchor of claim 1, further comprising a septum for preventing the fastener from being disengaged from the body.

7. The lead anchor of claim 1, wherein the fastener comprises a thread and the transverse lumen comprises a thread complementary to the thread of the fastener.

8. The lead anchor of claim 1, wherein the lead lumen comprises ridges formed on a surface of the lumen.

9. The lead anchor of claim 1, further comprising at least one suture channel formed in the exterior member and at least one suture eyelet formed in one of the suture tabs, wherein the at least one suture channel and the at least one suture eyelet are longitudinally aligned to permit a suture to wrap around the exterior member passing through the at least one suture eyelet and within the at least one suture channel.

10. The lead anchor of claim 1, wherein the sleeve extends out of both the first and second openings of the body.

11. An implantable stimulation device, comprising:
a lead having an electrode array; and
the lead anchor of claim 1, coupleable to the lead.

12. The implantable stimulation device of claim 11, further comprising:
a control module couplable to the lead.

13. The implantable stimulation device of claim 12, wherein the implantable stimulation device is a spinal cord stimulator.

14. The lead anchor of claim 1, wherein the body is made of metal or rigid plastic and the exterior member is made of silicone.

15. The lead anchor of claim 1, wherein the sleeve is removable from the lead lumen and the body.

16. A method of implanting a stimulation lead, the method comprising:
implanting an electrode array of the lead near tissue to be stimulated;
disposing the lead anchor of claim 1 around a portion of the lead by sliding the lead anchor along the lead to a desired anchoring position;
tightening the fastener using the tool to secure the lead anchor to the lead; and
securing the lead anchor to the surrounding tissue using sutures and the at least two suture tabs.

17. The method of claim 16, further comprising implanting a control module and coupling the electrode array to the control module using the lead.

18. The method of claim 16, wherein the at least two suture tabs comprises exactly two suture tabs.

19. The method of claim 16, wherein the at least two suture tabs extend from opposite sides of the exterior member in a staggered arrangement.

20. The method of claim 16, wherein the step of securing the lead anchor to the surrounding tissue comprises tying a suture to at least one of the at least two suture tabs, wherein the at least one suture tab includes a suture eyelet and the exterior member includes a suture channel, the suture channel and the suture eyelet are longitudinally aligned so that the suture wraps around the exterior member by passing through the suture eyelet and is at least partially disposed in the suture channel of the exterior member.

* * * * *